United States Patent [19]

McCoy

[11] Patent Number: 5,151,501
[45] Date of Patent: Sep. 29, 1992

[54] METHOD FOR SOLUBILIZATION AND NATURATION OF SOMATOTROPINS UTILIZING SULFOLANE

[75] Inventor: Kevin M. McCoy, Hoboken, N.J.

[73] Assignee: American Cyanamid Company, Stamford, Conn.

[21] Appl. No.: 811,494

[22] Filed: Dec. 20, 1991

[51] Int. Cl.$^5$ .................... C07K 3/12; C07K 15/06
[52] U.S. Cl. ..................... 530/399; 530/397; 530/403; 530/420; 530/410; 530/324
[58] Field of Search ............. 530/399, 403, 420, 410, 530/324

[56] References Cited

U.S. PATENT DOCUMENTS

| | | | |
|---|---|---|---|
| 4,511,502 | 4/1985 | Builder et al. | 530/399 |
| 4,694,073 | 9/1987 | Bentle et al. | 530/399 |
| 4,731,440 | 3/1988 | Bentle et al. | 530/399 |
| 4,923,967 | 5/1990 | Bobbitt et al. | 530/399 |
| 4,977,248 | 12/1990 | Creighton | 530/410 |
| 5,064,943 | 11/1991 | McCoy et al. | 530/399 |

OTHER PUBLICATIONS

Sharma, Separation Science and Technology, 21(8), 701–726, 1986.

Primary Examiner—Howard E. Schain
Attorney, Agent, or Firm—H. G. Jackson

[57] ABSTRACT

The present invention relates to a process for solubilization and naturation of somatotropins utilizing a combination of sulfolane and an aqueous alkaline solution. By utilizing the process of the present invention, enhanced yields of end product result.

15 Claims, No Drawings

METHOD FOR SOLUBILIZATION AND NATURATION OF SOMATOTROPINS UTILIZING SULFOLANE

BACKGROUND OF THE INVENTION

1. Field of the Invention

The present invention relates to the use of sulfolane in combination with an aqueous alkaline solution as a solubilization and naturation method for somatotropins.

2. Description of the Prior Art

Many methods for protein solubilization and naturation have been studied. In U.S. Pat. No. 4,511,503, refractile bodies are reported as insoluble granules of aggregated denatured somatotropin in the cytoplasm of the whole microorganism, E. Coli, in which they are produced. These refractile bodies are formed by overproduction of the specified protein of interest, such as somatotropin, as a result of genetically engineering the E. Coli cell to purposely overproduce that desired protein. The only mechanism by which to treat the refractile bodies is with a strong denaturant or chaotropic agent in order to cause the improperly folded molecules of both the desired protein product and the E. Coli proteins to unfold and become soluble. In addition to causing this denaturation, proteins must then be renatured in the proper monomeric form in order to be biologically active. This monomeric form is especially important for somatotropin. In order to obtain the active protein product, strong denaturants such as guanidine hydrochloride or urea at very high concentrations have been used.

As disclosed in U.S. Pat. No. 4,677,196 other chaotropic agents such as sodium dodecylsulfate (SDS) have also been used. Weak denaturants such as urea in concentrations of 3 to 5 molar have been used and are disclosed in U.S. Pat. No. 4,731,440. In U.S. Pat. No. 5,064,943 the deletion of urea is disclosed.

Each of the methods have certain associated problems with them. Guanidine hydrochloride is expensive and must be replaced during the naturation process in order for naturation to occur. Sodium dodecylsulfate is an effective denaturant and less expensive than guanidine hydrochloride, but it binds to the denatured protein so tightly that it makes complete removal from the protein difficult and increases processing costs. Urea is usually used as a weaker denaturant or chaotropic agent, but even methods utilizing urea have associated problems, such as contamination of the final product, handling, storage and waste treatment. Therefore, any method which uses no denaturant at all or low concentrations of a denaturant is specifically needed in the art. Methods for using no denaturant and for using low concentration of urea are disclosed in copending applications Ser. No. 07/285,477 filed Dec. 16, 1988, now U.S. Pat. No. 5,064,943 and Ser. No. 07/446,280 filed Dec. 5, 1989 respectively.

Additionally, it is the obtaining of this monomer product that is important in arriving at product proteins which have the physiological and biological activities of somatotropins. It is known that somatotropin monomer consists of approximately 191 amino acid residues and has a molecular weight of roughly 22,000 daltons. The monomer is not linked or noncovalently bonded to other similar monomer molecules.

In addition to the monomer form, somatotropins can exist in dimer form which means that two monomer molecules are covalently linked through intermolecular disulfide bonds or are noncovalently associated with one another. The dimer protein molecule consists of double the number of amino acids and double the molecular weight of monomer and is formed, unfortunately, by the inefficiencies of processes used to solubilize and renature the refractile bodies. In other words, it is formed by the isolation, naturation and purification process required to obtain active product protein from inactive inclusion (refractile) bodies combined within the microorganism cell.

The present invention provides a commercially feasible process for solubilizing proteins by effectively combining the use of sulfolane as a solubilizing agent with optimal naturation conditions used in aqueous dissolution procedures. Naturation includes oxidation of the cystine residues to form cysteine bonds. The use of sulfolane results in yield advantages when compared to the use of no denaturant, very low concentrations of urea or compared to other urea processes.

SUMMARY OF THE INVENTION

The present invention relates to the process for solubilization and naturation of somatotropins by using sulfolane in combination with an aqueous alkaline dissolution process in order to maximize monomer formation in the refractile body solubilization step, as part of an overall process for the production of purified recombinant somatotropin. This method comprises dispersing somatotropin refractile bodies in a 2.5 to 3.5 molar aqueous sulfolane solution for a sufficient time to solubilize said refractile bodies (2 to 20 minutes), at a pH necessary to dissolve said refractile bodies and then diluting said solution at least five fold with water. The resulting solution pH is adjusted to allow proper monomeric folding and oxidation of the somatotropin and given sufficient time for said monomeric folding and oxidation to occur.

It is an object of the present invention, therefore, to provide a process for solubilizing refractile bodies, especially those of somatotropin, by combining an aqueous alkaline dissolution process with sulfolane. The use of sulfolane has yield advantages over both the high urea concentration process known in the art and the low urea concentration process described in the copending application, as well as the no urea process described in the copending application. These and other objects of the invention will become apparent by the more detailed description of the invention provided herein below.

DETAILED DESCRIPTION OF THE INVENTION

The present invention relates to a method for solubilization and naturation of somatotropins comprising dispersing somatotropin refractile bodies into water containing about 2.5 to 3.5 M sulfolane; adjusting the pH of the refractile bodies in water to about 11.5 to 12.5 to effect solubilization; such that somatotropin protein concentration is about 2 to 10 g/L; holding said resulting solution at that pH and concentration for about 2 to 20 minutes; diluting with water; and adjusting the pH to 11.0 to 12.5, and a somatotropin content of about 0.4 to 2.0 g/L; maintaining the solution at the readjusted pH for a time sufficient to result in the somatotropin content in solution to be composed of properly folded monomeric somatotropin in good yield (approximately 5 to 10 hours).

"Somatotropin" as used herein denotes (1) animal growth hormone, derivatives, analogs and fragments of whatever species, for example, human, bovine, porcine, ovine, caprine, equine, avian(chicken, duck, goose, turkey), fish and others; (2) precursors to growth hormone, such as reduced (—SH) growth hormone and S-protected growth hormone, for example, growth hormone S-sulfonate; (3) variants of growth hormone or its precursors, for example, structures which have been modified to lengthen and/or shorten the growth hormone amino acid sequence, for example the 20 K variant of human growth hormone, methionyl human growth hormone, delta 7 and delta 9 porcine growth hormone and the like; and (4) analogs of growth hormone or its precursors, for example structures in which the growth hormone amino acid sequence has been modified by deletion or replacement of one or more amino acid residues. Both recombinantly derived somatotropin and naturally occurring somatotropin, as well as any other type of somatotropin, may be utilized in accordance with the present invention.

The first step in the novel method is the dispersal of the somatotropin refractile bodies into an aqueous solution of sulfolane (preferably deionized water) at a suitable concentration. Concentration of somatotropin is an important factor of the present invention and must be monitored to fall between 2 to 10 g/L. A suitable concentration of sulfolane is about 2.5 to 3.5 M and preferably about 3 M.

The pH of the concentrated somatotropin is adjusted to a range from about pH 11.5 to about pH 12.5, preferably about pH 12.0 to about pH 12.2 to solubilize the somatotropin in an aqueous sulfolane solution. Any strong base may be used to adjust the pH of the solution (e.g. the addition of sodium hydroxide or potassium hydroxide). This generally takes place in a relatively short period of time, about two to twenty minutes is typical. Then, this solution is diluted with water, preferably deionized water, which has been adjusted to about 11-12.5, at least three-fold, preferably five-fold (three to five-fold). Somatotropin concentration is now about 0.4 g/L to 2.0 g/L, with 0.8 to 1.2 g/L preferred.

After the concentrated dissolved somatotropin is diluted in the water, the pH may be readjusted to a range from about pH 11 to about pH 12.5. Lowering the pH increases the rate of naturation. The pH can be lowered by any suitable method, for example by the addition of phosphoric acid. The readjusted range is preferably about pH 11.3 to pH 12.0 for minimization of dimer. Especially preferred is a pH of 11.5 to 11.7.

It should also be stated that it is possible to dissolve the refractile bodies by dispersing them into an aqueous sulfolane solution that has already been pH adjusted to about 11.5-12.5 rather than adjusting the pH after dispersing the refractile bodies into the sulfolane solution. In fact, this is the preferred method of dissolving the refractile bodies. Also, the concentrated dissolved somatotropin may be added to the pH adjusted water to dilute it or the water may be added to the concentrated somatotropin solution. The former is the preferred method.

As shown in Table I, the sulfolane process results in higher monomer yield when compared to previously known processes involving 2 M urea, 4 M urea or totally aqueous.

TABLE I

COMPARISON OF MONOMER YIELDS FROM 2M UREA, 4M UREA, AQUEOUS, AND SULFOLANE PROCESSES MONOMER YIELD, %*

| Somatotropin | Sulfolane | 2M Urea | 4M Urea | Aqueous |
|---|---|---|---|---|
| Bovine | 81.1 (100) | 75.1 (93) | 67.0 (83) | 59.6 (73) |
| Porcine | 83.0 (100) | | | 67.8 (82) |

*Monomer Yield calculated as the ratio of 22K dalton somatotropin concentration as measured by gel permeation chromatography to total somatotropin concentration as measured by reverse phase HPLC. Percent monomer normalized to sulfolane process is shown in parenthesis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

BOVINE SOMATOTROPIN

Fermentation mash containing *E. Coli* cells which have been genetically modified to produce bovine somatotropin refractile bodies (also called inclusion bodies) is centrifuged to separate the cells from the broth. The cells are reslurried and disrupted using two passes at 8000 psig through a Gaulin homogenizer. The suspension is centrifuged and the pellet reslurried and treated with lysozyme and Triton X-100 detergent at 37° C. The suspension is centrifuged and the pellet is washed twice with water and is centrifuged after each wash.

The resulting pellet, containing the insoluble denatured bovine somatotropin (bST), is dispersed into deionized water at 25° C. The volume of water is chosen such that after sulfolane is added, somatotropin concentration is 5 g/L. Sulfolane is added until the concentration is 3 M. The pH is then adjusted to 12.0 by addition of 1 N sodium hydroxide resulting in visible dissolution of the inclusion bodies. After twenty minutes, the solution is then diluted into four volumes of pH 11.5 deionized water, the pH is adjusted to 11.5 if necessary, and aged for five hours. After dilution the somatotropin concentration is 1 g/L.

At the end of aging the pH of the solution is lowered to 10.8 using 1 M phosphoric acid. The solution is ultrafiltered and diafiltered on a 100 K dalton cut-off hollow-fiber cartridge such as an Amicon H26P100-43. The permeate is then concentrated using a 5 K dalton cut-off spiral-wound cartridge ultrafilter such as Koch K-131A.

The concentrated solution is adjusted to pH 9 using 1 M phosphoric acid and applied at 15 g bST per L resin to an anion-exchanger such as DEAE-Sepharose Fast Flow which has been equilibrated with 10 mM borate, pH 9. After washing with the equilibration buffer, the bST is eluted using a 100 mM NaCl, 10 mM borate solution, at pH 9. The bST peak is concentrated and desalted with an ammonia solution using an ultrafilter with 10 K dalton cut-off cassettes such as Millipore Pellicon until the conductivity of the permeate is less than 300 microsiemens/cm. The desalted solution at approximately 100 g/L is lyophilized to yield bovine somatotropin (bST) which passes established biological and chemical tests. The yield of lyophilized bovine somatotropin is 48% from the fermentation broth.

EXAMPLE 2

PORCINE SOMATOTROPIN

Fermentation mash containing *E. Coli* cells which have been genetically modified to produce porcine somatotropin (pST) inclusion bodies is treated by the same procedure as described in the first paragraph of Example 1.

The resulting pellet, containing the insoluble denatured porcine somatotropin (pST), is dispersed into deionized water at 25° C. The volume of the water is chosen such that after the sulfolane is added the somatotropin concentration will be 5 g/L. Sulfolane is added until the concentration is 3 M. The pH is then adjusted to 12.0 by addition of 1 N sodium hydroxide resulting in visible dissolution of the inclusion bodies. After twenty minutes the solution is then diluted into four volumes of pH 11.5 deionized water and the pH adjusted to 11.5 if necessary, and aged for five hours. After dilution into four volumes of pH 11.5 water, the somatotropin concentration is 1 g/L. The yield of pST monomer is 83% relative to total pST available.

What is claimed is:

1. A process for solubilization and naturation of somatotropins, said process comprising: dispersing somatotropin refractrile bodies in an aqueous solution of about 2.5 to 3.5 M sulfolane at a pH and for sufficient time to solubilize said refractile bodies and then diluting said solution at least three-fold with water at a pH and for a time sufficient to result in properly folded monomeric somatotropin.

2. A process according to claim 1, wherein said time to solubilize said refractile bodies is about 2 to 20 minutes.

3. A process according to claim 1, wherein said pH is 11.0 to 12.5.

4. A process according to claim 1, wherein said time sufficient to result in properly folded monomeric somatotropin is 5 to 10 hours.

5. A process according to claim 1, wherein said somatotropin is human, bovine, porcine, ovine, equine, caprine, fish or avian somatotropin.

6. A process according to claim 1, wherein said somatotropin is bovine somatotropin.

7. A process according to claim 1, wherein said somatotropin is porcine somatotropin.

8. A process according to claim 1, additionally comprising: adding to the sulfolane solution, prior to the dilution with at least three-fold water, a reducing agent.

9. A process according to claim 8, wherein said reducing agent is beta-mercaptoethanol, dithiothreitol or combinations thereof.

10. A process according to claim 9, wherein said somatotropin is human, bovine, porcine, ovine, equine, caprine, fish or avian somatotropin.

11. A process according to claim 10, wherein said somatotropin is bovine or porcine somatotropin.

12. A process for the isolation and purification of recombinantly-produced somatotropin, said process comprising: washing refractile bodies containing said somatotropin and other proteins with water; dissolving said refractile bodies at pH 11.0 to 12.5 in about 2.5 to 3.5 M sulfolane such that the somatotropin concentration is about 2 to 10 g/L; holding said solution at said pH for about two to twenty minutes; diluting said solution at least three-fold with water; adjusting the pH of the said diluted solution to 11.3 to 12.0, such that the sulfolane concentration is about 3 M and the somatotropin concentration is about 0.4 to 2.0 g/L; and holding said solution for 5 to 10 hours.

13. A process according to claim 12, wherein said somatotropin is human, bovine, porcine, ovine, equine, caprine, fish or avian somatotropin.

14. A process according to claim 13, wherein said somatotropin is bovine or porcine somatotropin.

15. A process according to claim 14, wherein said time is 7 to 8 hours.

* * * * *